United States Patent [19]
Snow et al.

[11] Patent Number: 6,017,997
[45] Date of Patent: Jan. 25, 2000

[54] WATERBORNE POLYURETHANE HAVING FILM PROPERTIES COMPARABLE TO RUBBER

[75] Inventors: George E. Snow, Medina; Tina R. Dame, Brunswick, both of Ohio

[73] Assignee: The B. F. Goodrich Company, Richfield, Ohio

[21] Appl. No.: 08/962,435

[22] Filed: Oct. 31, 1997

[51] Int. Cl.$^7$ .............. C08J 3/00; C08K 3/20; C08L 75/00; C08G 18/00

[52] U.S. Cl. .............. 524/591; 2/159; 2/161.7; 2/168; 428/423.1; 524/589; 524/590; 524/839; 524/840; 528/44

[58] Field of Search ............ 524/591, 839, 524/840, 589, 590; 528/44; 428/423.1; 604/349, 264; 2/159, 161.7, 168

[56] References Cited

U.S. PATENT DOCUMENTS

| | | | |
|---|---|---|---|
| 2,621,166 | 12/1952 | Schmidt et al. | 260/75 |
| 2,625,535 | 1/1953 | Mastin et al. | 260/75 |
| 2,729,618 | 1/1956 | Müller et al. | 260/75 |
| 2,770,612 | 11/1956 | Schollenberger | 260/75 |
| 2,843,568 | 7/1958 | Benning et al. | 260/75 |
| 2,861,972 | 11/1958 | Müller et al. | 260/45.4 |
| 2,871,218 | 1/1959 | Schollenberger | 260/45.4 |
| 2,899,411 | 8/1959 | Schollenberger | 260/77.5 |
| 2,901,467 | 8/1959 | Croco | 260/77.5 |
| 2,968,575 | 1/1961 | Mallonee | 106/287 |
| 2,998,403 | 8/1961 | Müller et al. | 260/45.4 |
| 3,001,971 | 9/1961 | Scott et al. | 260/47 |
| 3,012,992 | 12/1961 | Pigott et al. | 260/75 |
| 3,016,364 | 1/1962 | Müller | 260/47 |
| 3,382,138 | 5/1968 | Barth | 161/190 |
| 3,411,982 | 11/1968 | Kavalir et al. | 161/242 |
| 3,422,066 | 1/1969 | Britain | 260/47 |
| 3,577,385 | 5/1971 | Feltzin et al. | 260/47 |
| 3,591,561 | 7/1971 | Kazama et al. | 260/77.5 |
| 3,664,979 | 5/1972 | Tanomura et al. | 260/75 |
| 3,684,770 | 8/1972 | Meisert et al. | 260/75 |
| 3,689,443 | 9/1972 | Fensch | 260/18 |
| 3,804,812 | 4/1974 | Koroscil | 260/77.5 |
| 3,813,695 | 6/1974 | Podell, Jr. et al. | 2/168 |
| 3,846,378 | 11/1974 | Griswold | 260/77.5 |
| 3,872,515 | 3/1975 | Miner et al. | 2/168 |
| 3,879,764 | 4/1975 | Weber-Leil | 2/167 |
| 3,883,899 | 5/1975 | Ganz | 2/168 |
| 4,064,564 | 12/1977 | Casey | 2/168 |
| 4,131,604 | 12/1978 | Szycher | 528/79 |
| 4,255,552 | 3/1981 | Schollenberger et al. | 528/50 |
| 4,284,750 | 8/1981 | Amirsakis | 528/79 |
| 4,408,008 | 10/1983 | Markusch | 524/591 |
| 4,463,156 | 7/1984 | McGary, Jr. et al. | 528/65 |
| 4,877,856 | 10/1989 | Hall et al. | 528/44.79 |
| 5,075,370 | 12/1991 | Kubitza et al. | 524/591 |
| 5,086,110 | 2/1992 | Xiao et al. | 524/840 |
| 5,354,807 | 10/1994 | Dochniak | 524/591 |
| 5,458,936 | 10/1995 | Miller et al. | 428/35.7 |
| 5,576,072 | 11/1996 | Hostettler et al. | 427/532 |

FOREIGN PATENT DOCUMENTS

| | | |
|---|---|---|
| 0148970 | 7/1985 | European Pat. Off. . |
| 0342826 | 11/1989 | European Pat. Off. . |
| 0426883 | 5/1991 | European Pat. Off. . |
| 0741152 | 11/1996 | European Pat. Off. . |
| 1645040 | 9/1970 | Germany . |
| 1570241 | 2/1972 | Germany . |
| 58-206619 | 12/1983 | Japan . |
| 1149771 | 4/1969 | United Kingdom . |
| 1154159 | 6/1969 | United Kingdom . |

OTHER PUBLICATIONS

American Society for Testing and Materials, Designation: D2370–82, "Standard Test Method for Tensile Properties of Organic Coatings", pp. 441–444.

Brochure, Bayer Corporation, "Product Index Raw Materials for High–Performance Coatings", 1996.

Brochure, Cytec, "Developing TMXDI® (META) Aliphatic Isocyanate for Aqueous Polyurethane Dispersions", pp. 1–37.

Brochure, "Zeneca Resins Product Guide for Coating Resins", pp. 1–16.

*Primary Examiner*—Patrick D. Niland
*Attorney, Agent, or Firm*—George W. Moxon II

[57] ABSTRACT

A waterborne dispersion of a polyurethane polymer is disclosed, which is useful as a film having improved mechanical properties. More particularly, the film has properties comparable to rubber; including, a percentage elongation greater than 700%; a tensile strength greater than 3500 psi; a 100% modulus below 450 psi; a 300% modulus below 700 psi; and, a 500% modulus below 1500 psi. The film can be prepared in the absence of a solvent, thus making it attractive for a variety of protection products for medical and industrial applications such as gloves, condoms, catheters, and the like. The polymer is useful as a coating for textiles, such as backcoatings, fabric or fiber saturants, finishes, or transfer coatings, or other textile and non-textile applications where good elastomeric properties would be useful.

61 Claims, No Drawings

WATERBORNE POLYURETHANE HAVING FILM PROPERTIES COMPARABLE TO RUBBER

BACKGROUND OF THE INVENTION

1. Field of the Invention

This invention relates to a waterborne polyurethane. More particularly, the invention relates to a waterborne polyurethane useful as a film, the film having improved properties comparable to or even exceeding those of rubber, i.e., a percentage elongation greater than 700%, a tensile strength greater than 3500 psi, a 100% modulus below 450 psi, a 300% modulus below 700 psi, and a 500% modulus below 1500 psi.

2. Description of the Prior Art

Many medical devices, particularly protective products, devices and films such as gloves for medical and industrial applications, contraceptive devices, catheters, balloons, cuffs, wound care, and various tubing are manufactured from materials having elastomeric properties. By "elastomeric properties" it is meant that the substance can be stretched at room temperature to at least twice its original length, and, after having been stretched and the stress removed, returns with force to approximately its original length within a short time.

A material having elastomeric properties is also known as an elastomer—the generic term for a rubber. A rubber is defined as a natural, synthetic, or modified high polymer with elastic properties, and, after vulcanization, elastic recovery. The terminology "rubber" is meant to include both natural rubber and synthetic rubber—denoted cis-1,4-polyisoprene, which has extensively been used in the past in the manufacture of many goods, including the aforementioned protective products, devices, and films. Typically, the rubber is initially available as a rubber latex, i.e., a colloidal suspension of the rubber in an aqueous medium, which is then used in the production of the rubbery material.

Use of a rubber latex to manufacture these articles can be problematic from several different perspectives. Because rubber latex is a natural product, it is subject to inherent variations and inconsistencies, which require compensation during the manufacturing process in order to maintain adherence to process and performance requirements. The rubber latex is also susceptible to bacterial degradation, which requires the manufacturer to periodically clean out the process and scrap such material.

Further, the number of latex allergy incidents has been growing rapidly since 1989. In that year, the FDA received its first reports of patients, who when exposed to natural latex medical devices, died from anaphylactic shock. An estimated 15% of the healthcare worker population and a small percentage of the overall population are now sensitive to natural latex. The immunoglobulin E (IgE) latex allergy can manifest itself in three types of reactions;

Type IV: Delayed hypersensitivity (allergic contact dermatitis)

Type II: Irritation (non-allergic)

Type I: Immediate Hypersensitivity (allergic)

The most common allergic response is type IV, a type of contact dermatitis caused by not only the protein in natural rubber latex, but by the additives which improve its properties. These additives include sulfur and sulfur based chemicals and accelerators, mercaptobenzothiazoles, thiurams, carbamates, and phenylene diamines. The type I is the most serious, and possibly fatal, allergic response.

Because of these past problems associated with the manufacture and use of rubber, polyurethane materials have been substituted for rubber in some applications. Polyurethanes are advantageous because they can be biocompatible, can be formed into films with high water vapor transmission, are cooler to wear, and are oil resistant and do not swell in the presence of body oils.

Use of these prior art polyurethane materials, though, has been problematic for several reasons. For example, many of these materials must be extruded, thermoformed or solubilized in an organic solvent to be shaped for use. Further, many of these prior art polyurethane materials are synthesized using a solvent, which can be detrimental if the resultant polyurethane material is used in applications necessitating a solvent-free polyurethane, i.e., protective devices such as condoms, gloves, and catheters. Thus, both safety and environmental considerations have necessitated a search for a waterborne, water-soluble, solvent-free polyurethane.

Also, these prior art waterborne polyurethane materials have been mechanically deficient in that they have not yielded a film having the requisite combination of high tensile strength, high percentage elongation and low modulus characteristic of natural or synthetic rubber. For example, TABLE I below, shows typical values of tensile strength, percentage elongation, and modulus for natural rubber.

TABLE I

| PROPERTY | NATURAL RUBBER |
| --- | --- |
| Tensile strength, psi | 4800 |
| Elongation, % | 840 |
| 100% Modulus, psi | 125 |
| 300% Modulus, psi | 200 |
| 500% Modulus, psi | 600 |
| 750% Modulus, psi | 2700 |

Waterborne prior art polyurethane materials, on the other hand, have not yielded the requisite combination of high tensile strength, high percentage elongation and low modulus characteristic of the natural or synthetic rubber set out in TABLE I.

Thus, there is a need for a solvent-free, or low solvent containing waterborne polyurethane, which can be used in the production of a film having a balance of high tensile strength, high percentage elongation and low modulus. The polyurethane film must have elastomeric properties like those attributed to rubber—that is, it must stretch under tension, have high tensile strength, retract rapidly, and give nearly complete recovery to its original dimensions.

BRIEF SUMMARY OF THE INVENTION

The present invention provides a waterborne polyurethane useful as a film having elastomeric properties. More particularly, the film has a percentage elongation greater than 700%, a tensile strength greater than 4500 psi, a 100% modulus below 450 psi, a 300% modulus below 700 psi, and a 500% modulus below 1500 psi. The polyurethane can preferably be prepared in the absence of an organic solvent or in low solvent content media.

According to a first aspect of the invention, a waterborne polyurethane dispersion having elastomeric properties is provided. The polyurethane comprises the reaction product of (a) a polyisocyanate component; (b) an active hydrogen containing component, such as a polyol or a polyamide; and (c) a water-solubilizing compound having water-solubilizing groups to form an isocyanate terminal prepolymer, which is neutralized by reaction with a tertiary amine, dispersed in water, and the reaction product is then chain extended by reaction with a primary or secondary amine. The polyurethane dispersion is capable of forming a film having a tensile strength greater than about 3500 psi and a percentage elongation greater than about 700%. The polyurethane is prepared in a low cosolvent system, preferably in the absence of an organic solvent.

According to a second aspect of the invention, a waterborne polyurethane for use as a film having elastomeric properties is provided, the film having a tensile strength greater than about 3500 psi and a percentage elongation greater than about 700%. The film also has a 100% modulus below 450 psi, 300% modulus below 700 psi, and a 500% modulus below 1500 psi.

According to a third aspect of the invention, a film cast from a waterborne polyurethane dispersion is provided, the film having a percentage elongation greater than about 700% and a tensile strength greater than about 4500 psi. The film may be used in the manufacture of various products, particularly medical gloves, regular gloves, catheters, tubing and condoms, and the like products, which would benefit from being made from a polymer having the characteristics of the polymer of the present invention.

One advantage of the present invention is that a waterborne polyurethane dispersion can be used to produce a film having elastomeric properties.

Another advantage of the present invention is that a solvent-free waterborne polyurethane dispersion can be used to produce certain medical products, including gloves and condoms.

Another advantage of the present invention is that a waterborne polyurethane dispersion can be used to produce a film having both a percentage elongation greater than 700% and a tensile strength greater than 4500 psi.

Still another advantage of the present invention is that an elastomeric film cast from a polyurethane dispersion can be simply and economically manufactured.

Still another advantage of the present invention is that a waterborne polyurethane can be used to produce a film having mechanical properties comparable to rubber. Still another advantage of the present invention is that certain medical products, particularly gloves, condoms, catheters, and tubing can be produced from a material other than rubber.

Still a further advantage of the present invention is that a wide array of products can be simply and economically manufactured using an elastomeric film cast or dipped from a waterborne polyurethane dispersion or by using the polymer, i.e., the waterborne polyurethane dispersion, as a coating for textiles, such as backcoatings, fabric or fiber saturants, finishes, or transfer coatings, or other textile and non-textile applications where good elastomeric properties would be useful.

Still other benefits and advantages of the invention will become apparent to those skilled in the art upon a reading and understanding of the following detailed specification.

DETAILED DESCRIPTION OF THE PREFERRED EMBODIMENT

The present invention relates to a waterborne polyurethane polymer demonstrating film properties comparable to rubber. The waterborne polyurethane can be stabilized anionically, cationically, or non-ionically. The films of the present invention show elastic properties, i.e., mechanical properties comparable to rubber, including, when run at a gage length of one inch, a percentage elongation of greater than 700%; a tensile strength greater than 4500 psi; a 300% modulus below 700 psi; a 500% modulus below 1500 psi; little to no yield point; and, rapid recovery to original shape after stretching. Rubber-like properties (or comparable properties) are attributable to a film which can be stretched at room temperature to at least twice its original length and after having been stretched and the stress removed, will return with force to approximately its original length within a short time.

The terminology "percentage elongation", "tensile strength", "modulus of elasticity" and "yield point" are well-known to those skilled in the art. These are measured in accordance with ASTM (American Society for Testing and Materials) Standard D 2370-82. Percentage elongation is the fractional increase in a material's length due to stress in tension. Tensile strength is the maximum stress a material subjected to a stretching load can withstand without tearing. The modulus of elasticity is the ratio of the increment of some specified form of stress to the increment of some specified form of strain. Yield point is the lowest stress at which strain increases without increase in stress.

The waterborne polyurethane polymer of the present invention is synthesized by reacting a polyisocyanate with an active hydrogen containing, high molecular weight product, such as a long-chain polyol or a long-chain polyamide, and a water-solubilizing compound having water-solubilizing groups to form an isocyanate terminal prepolymer. The prepolymer is subsequently neutralized with a tertiary amine and dispersed in water. The dispersed prepolymer is then chain-extended using a functional primary and/or secondary amine having at least 2 active hydrogens.

Any organic polyisocyanate is believed to be suitable for use in the present invention. Particular isocyanates include aliphatic, cycloaliphatic, araliphatic, and aromatic polyisocyanates, used alone or in mixtures of two or more. The preferred polyisocyanate is a diisocyanate.

Specific examples of suitable aliphatic polyisocyanates include alpha,omega-alkylene diisocyanates having from 5 to 20 carbon atoms, for instance, hexamethylene 1,6-diisocyanate, 1,12-dodecane diisocyanate, 2,2,4-trimethyl-hexamethylene diisocyanate, 2,4,4-trimethyl-hexamethylene diisocyanate, 2-methyl-1,5-pentamethylene diisocyanate, and mixtures thereof.

Specific examples of suitable cycloalipahtic polyisocyanates include dicyclohexlymethane diisocyanate (commercially available as Desmodur™W from Bayer Coating Division), isophorone diisocyanate, 1,4-cyclohexane diisocyanate, 1,4-cyclohexane bis(methylene isocyanate), 1,3-bis(isocyanatomethyl) cyclohexane, and mixtures thereof.

Specific examples of suitable araliphatic polyisocyanates include m-tetramethyl xylylene diisocyanate, p-tetramethyl xylylene diisocyanate, 1,4-xylylene diisocyanate, 1,3-xylylene diisocyanate and mixtures thereof.

Examples of suitable aromatic diisocyanates include methane-bis(4-phenyl isocyanate), toluene diisocyanate and their isomers.

The preferred polyisocyanate is an aliphatic diisocyanate. Isophorone diisocyanate (IPDI) and an isomer blend of 2,2,4 and 2,4,4 trimethyl hexamethylene diisocyanate (TMDI), are the aliphatic diisocyanates of choice because of their inherent "softness" (low modulus films), low prepolymer viscosity for reduced co-solvent levels, and relatively high tensile strength capabilities. Other polyisocyanates may be used in whole or in part substitution to attain similar properties, but will lessen certain polymer qualities. For example, tetramethylxylene diisocyanate (TMXDI) decreases tensile strength. Cyclohexyl bis-methylenisocyanate ($H_{12}$MDI) and methane-bis(4-phenyl isocyanate)(MDI) increase modulus. Toluene diisocyanate (TDI) works in the present invention if non-yellowing properties are not required.

The terminology "polyol" denotes any high molecular weight product, which has an active hydrogen component that can be reacted and includes materials having an average of about two or more hydroxyl groups per molecule. The long-chain polyol which can be used in the present invention includes higher polymeric polyols such as polyester polyols and polyether polyols, as well as other acceptable "polyol" reactants, which have an active hydrogen component such as polyester polyols, polyhydroxy polyester amides, hydroxyl containing polycaprolactones, hydroxy-containing acrylic interpolymers, hydroxy-containing epoxies, and hydrophobic polyalkylene ether polyols.

The polyester polyols are esterification products prepared by the reaction of organic polycarboxylic acids or their anhydrides with a stoichiometric excess of a polyol. Examples of suitable polyols for use in the reaction include polyglycol adipates, polyethylene terepthalate polyols, polycaprolactone polyols, orthophthalic polyols, and sulfonated polyols, etc.

The polycarboxylic acids and polyols are typically aliphatic or aromatic dibasic acids and diols. The diols used in making the polyester include alkylene glycols, e.g., ethylene glycol, butylene glycol, neopentyl glycol and other glycols such as bisphenol A, cyclohexane diol, cyclohexane dimethanol, caprolactone diol, hydroxyalkylated bisphenols, and polyether glycols.

Suitable carboxylic acids include dicarboxylic acids and tricarboxylic acids, e.g., maleic acid, succinic acid, glutaric acid, adipic acid, pimelic acid, azelaic acid, sebacic acid, chlorendic acid, 1,2,4-butane-tricarboxylic acid, phthalic acid, terephthalic acid, and the isomers of phthalic acid.

Preferably, the polyester polyol should be as non-crystalline as possible and in that regard should have a broad melting range and be liquid at 90° F. or lower. The average molecular weight for the polyester polyol should be at least 2400 to afford high elongation and low tensile modulus at a given elongation. The preferred molecular weight for the polyols and polyamides used in this invention is from about 2900 to about 5500 Daltons.

The preferred polyester polyol is a diol. More particularly, it is a hexane diol neopentyl glycol adipic acid polyester diol—e.g., 67-3000 HNA (Pioneer Plastics) and 67-1000 HNA (Pioneer Plastics). Other preferred polyester diols include Rucoflex® 1015-35 (RUCO Polymer Corp.) and Rucoflex® 1043-35 (RUCO Polymer Corp.).

Polyether diols may be substituted in whole or in part; however, larger amounts of polyether diols tend to lower tensile strength. The use of the Acclaim® 3201 series (Arco Chemical), an improved polyether diol with a lower monol content, does not significantly reduce tensile strength as would conventional polyether diols. In addition, these polyether diols give significantly lower prepolymer viscosities, which allow for the manufacture of cosolvent free, low modulus urethanes.

Instead of a long-chain polyol, a long-chain amine may also be used in the practice of the present invention. Suitable amines include: Jeffamine® D-2000 and D-4000, which are amine-terminated polypropylene glycols, differing only by molecular weight, and which are available from Huntsman Chemical Company. It is also recognized that other difunctional active hydrogen containing materials in a suitable molecular weight range (averaging from about 2500 to about 5500 amu), may be suitable for this application.

To enhance the water-solubility, a water-solubilizing compound bearing a group that is water-soluble or can be made water-soluble is incorporated into the polymer chain. One particularly preferred water-solubilizing compound is 2,2-bis(hydroxymethyl) propionic acid—also known as dimethylol propanoic acid (DMPA). Other suitable water-solubilizing compounds would include the following: tartaric acid, dimethylol butanoic acid (DMBA), glycollic acid, thioglycollic acid, lactic acid, malic acid, dihydroxy malic acid, dihydroxy tartaric acid, and 2,6-dihydroxy benzoic acid.

Water-solubilizing groups are incorporated in the prepolymer in an inactive form in the water-solubilizing compound and activated by a salt-forming compound such as a tertiary amine. The water-solubilizing groups are hydrophilic or ionic groups whose presence in the polymer assists solubility or dispersability of the polymer in water and enhances the stability of polymer dispersions. Polyurethanes are generally hydrophobic and not water-dispersable.

The formation of the isocyanate terminal prepolymer may be achieved without the use of a catalyst. However, a catalyst is preferred. Examples of suitable catalysts include stannous octoate, dibutyl tin dilaurate and tertiary amine compounds such as triethyl amine and bis (dimethylaminoethyl) ether, morpholine compounds such as β,β'-dimorpholinodiethyl ether, bismuth carboxylates, zincbismuth carboxylates, iron (III) chloride, potassium octoate, potassium acetate, and DABCO® (bicycloamine). The preferred catalyst is FASCAT® 2003 from Atochem. The amount of catalyst used is typically 10–40 parts per million of the isocyanate terminal prepolymer.

A prepolymer diluent may be used to render the viscosity of the copolymer dispersion low enough to process the product. The preferred prepolymer diluent is N-methyl pyrrolidinone (NMP), because it does not contain reactive groups, which will interfere with the reaction. It is preferred that a minimal amount of the N-methyl pyrrolidinone (NMP) be used, preferably in a range of 0–10% N-methyl pyrrolidinone (NMP) by weight of the polyurethane dispersion. The maximum amount of N-methyl pyrrolidinone (NMP) used is preferably 10.0% by weight of the resultant waterborne polyurethane dispersion.

However, the copolymer dispersion is preferably prepared in the absence of a diluent. In this case, the prepolymer should be made in a way that will minimize its resultant viscosity. In neat (no solvent) and solution polymers, viscosity is largely determined by the molecular weight of the polymer. To minimize the molecular weight of a finished prepolymer, an NCO/OH ratio of 2/1 should be used. In this way the diol portions are essentially endcapped by the diisocyanate species, leaving an isocyanate terminal prepolymer of relatively low viscosity. As the NCO/OH ratio of a prepolymer is reduced, the resultant viscosity increases dramatically. It is recognized that cosolvent free materials can be made at below 2/1 NCO/OH ratios, but they become more difficult to process, pump, stir, etc. Also, higher temperatures will be needed to work with such a prepolymer.

As the NCO/OH ratio of a prepolymer is increased above 2/1, the molecular weight will be limited as with the 2/1 ratio, but the excess diisocyanate will function as a diluent, further reducing viscosity. While this is a desired effect, raising the NCO/OH ratio above 2/1 can also have negative effects. When isocyanate content of a polyurethane is increased, the hardness, or modulus of the polyurethane, along with the yield point, is increased. This is undesirable for producing a "rubbery" polymer. Also, when excess diisocyanate (obtained from using an NCO/OH ratio much greater than 2/1) is introduced into a dispersion, and this dispersion is then extended with a primary (or secondary) amine, high molecular weight polyureas may be formed. These materials are not soluble, but by controlling the ratio in the range of 1.8 to 2.3 the results will be satisfactory. If an excess of isocyanate is used the result may be gels or grittiness in a cast film, and sediment in the dispersion. This can lead to weakened films, which have a poor appearance. For these reasons, an NCO/OH ratio of about 1.8/1 to 2.3/1 are desirable, and ratios of about 1.9/1 to 2.1/1 are most desirable.

Another important factor in keeping prepolymer viscosity low is in the selection of raw materials, and the amounts in which they are used. The preferred isocyanates for this invention are isophorone diisocyanate and 2,2,4 and/or 2,4,4, trimethyl hexamethylene diisocyanate, due to their positive effects (high strength, low modulus, low prepolymer viscosity) on processing and film properties. To further reduce prepolymer viscosity, a polyether polyol may be substituted in whole or in part for a polyester polyol. The preferred polyether polyol is Acclaim 3201, due to its low viscosity when reacted into a prepolymer, and due to its low monol content vs. conventional polyethers.

The acid content of the water-solubilizing compound is yet another consideration for producing a low viscosity prepolymer. Higher acid numbers will lead to higher viscosity, but there is also a minimum amount of acid needed to render a given polyurethane backbone dispersable. The preferred carboxyl containing diol in this invention is dimethylol propionic acid. The preferred range of carboxyl containing diol or water-solubilizing compound is from about 2 wt. % to about 4 wt. % of the total prepolymer. The amount used will approach 2 wt. % as the backbone becomes more hydrophilic, as with higher concentrations of polyether diol. As the backbone becomes more hydrophobic, as with polyester based systems, the acid content needed for dispersion will approach 3–4 wt. %.

Neutralization of the prepolymer having dependent carboxyl groups with the tertiary amine converts the carboxyl groups to carboxylate anions, thus having a solubilizing effect. Suitable tertiary amines, which can be used to neutralize the polymer include triethyl amine (TEA), dimethyl ethanol amine (DMEA), and N-methyl morpholine. The preferred tertiary amine is triethyl amine (TEA). It is recognized that primary or secondary amines may be used in place of tertiary amines, if they are sufficiently hindered to avoid interfering with the chain extension process.

As a chain extender, any organic 2+ (i.e., having 2 or more) functional primary and/or secondary amine would be suitable for use in the present invention. Suitable organic amines for use as a chain extender include di-ethylene tri-amine (DETA), ethylene diamine (EDA), meta-xylylene diamine (MXDA), and aminoethyl ethanolamine (AEEA). Also suitable for practice in the present invention are propylene diamine, butylene diamine, hexamethylene diamine, cyclohexylene diamine, phenylene diamine, tolylene diamine, xylylene diamine, 3,3-dichlorobenzidene, 4,4-methylene-bis (2-chloroaniline), and 3,3-dichloro-4,4-diamino diphenylmethane.

Hydrazine, an inorganic amine, is preferably used to finish off any excess extension necessary. Other suitable inorganic amines would include ammonia, substituted hydrazines, and hydrazine reaction products.

A degree of branching of the polymer may be beneficial, but is not required to maintain a high tensile strength and improve resistance to creep—that is, recovery to that or near its original length after stretching. This degree of branching may be accomplished during the prepolymer step or the extension step. For branching during the extension step, the chain extender DETA is preferred, but other 2+ (two or more) functional amines may also be used in conjunction with ring-structured diamines, e.g., Metaxylenediamine (MXDA).

For pre-polymer branching, it is preferred that trimethylol propane (TMP) and other 2+ functional diols be used. Higher functional 2+ isocyanates may alternatively be used.

The branching monomers should be present in amounts from about 0.5 wt. % to 4 wt. % of the polymer backbone. Preferably, the requisite degree of branching needed is obtained during the extension step rather than during the prepolymer step. Otherwise, the high viscosity of the prepolymer, which results due to the branching, must be accounted for during the extension step.

The invention will now be described in detail in the following examples.

EXAMPLE I

Prepolymer Step

The following materials were charged to a reactor: 2039.92 grams (0.474 eq.) 67-3000 HNA (Pioneer Plastics); and 59.47 grams (0.046 eq.) 67-1000 HNA (Pioneer Plastics). The mixer was then turned on and 530.35 grams (1.70 eq.) of isophorone diisocyanate (IPDI) was added to the reactor. At this point, heat was applied to the batch to raise the temperature to over 200° F. After about 35 minutes at over 200° F., 480 grams of N-methyl pyrrolidinone (NMP), followed by 90.26 grams (0.48 eq.) dimethylol propanoic acid (DMPA) were charged. The resultant mixture was allowed to react for about two hours, at about 190–200° F. The percent NCO remaining was then measured using a titration with dibutylamine (DBA) and 1.0M HCl. The result is a finished prepolymer which may be immediately extended, as set forth below, or stored under a nitrogen cap at 120° F.

Extension Step 600 grams of the prepolymer were warmed to 142° F. and 15.34 grams triethyl amine (TEA) were charged to the batch. When the TEA was thoroughly mixed, 512.8 grams of the prepolymer were charged to a vessel containing 412 grams water at 82° F. 12.05 grams N-methyl pyrrolidinone (NMP) were charged to the batch and allowed to mix for 15 minutes. Chain extension was then accomplished by charging a blend containing 4.47 grams meta-xylene diamine (MXDA)/2.26 grams diethylenetriamine (DETA)/15.72 grams $H_2O$. A small amount of hydrazine (3.58 grams) was added to complete chain extension. The result is a polymer which can be used or stored under a nitrogen cap.

EXAMPLE II

The finished prepolymer of Example I was also chain extended as shown below.

Extension Step 600 grams of the prepolymer of Example I were warmed to 144° F. and 15.34 grams of TEA were charged to the batch. When the TEA was thoroughly mixed, 512.8 grams of the prepolymer were charged to a vessel containing 414 grams water at 78° F. 12.05 grams of NMP were charged to the batch and allowed to mix for 15 minutes. Chain extension was then accomplished by charging a blend containing 2.68 grams of MXDA, 1.36 grams of DETA, and 9.44 grams of $H_2O$. A small amount of hydrazine (3.75 grams) was added to complete chain extension. The result is a polymer product.

EXAMPLE III

Prepolymer Step

The following materials were charged to a reactor: 1883.51 grams (0.450 eq.) 1015-35 (RUCO Polymer Corp.); and 84.67 grams (0.070 eq.) 67-1000 HNA (Pioneer Plastics). The mixer was then turned on and 497.20 grams (1.70 eq.) of IPDI was added to the reactor. At this point, heat was applied to the batch to raise the temperature to over 200° F. Once the exotherm began to subside, three drops FASCAT® 2003 (Atochem) catalyst were charged. After about thirty minutes at over 200° F., 450 grams of NMP, followed by 84.62 grams (0.48 eq.) DMPA were charged. The resultant mixture was allowed to react for about two hours at about 190–200° F. The percent NCO remaining was then measured using a titration with DBA and HCl. The result is a finished prepolymer.

Extension Step 800 grams of the prepolymer were warmed to 142° F. and 20.45 grams triethyl amine (TEA) were charged to the batch. When the TEA was thoroughly mixed, 717.4 grams of the prepolymer were charged to a vessel containing 586 grams water at 97° F. 16.87 grams N-methyl pyrrolidinone (NMP) were charged to the batch and allowed to mix for 15 minutes. Chain extension was then accomplished by charging a blend containing 8.72 grams meta-xylene diamine (MXDA)/8.82 grams DETA/17.54 grams $H_2O$. The result is a polymer product.

EXAMPLE IV

Prepolymer Step

The following materials were charged to a reactor: 408.09 grams (0.450 eq.) 1015-35 (RUCO Polymer Corp.) and 18.35 grams (0.070 eq.) 67-1000 HNA (Pioneer Plastics). The mixer was then turned on and 107.73 grams (1.70 eq.) of isophorone diisocyanate (IPDI) was added to the reactor. At this point, heat was added to the batch to raise the temperature to over 200° F. Once the exotherm began to subside, one drop FASCAT® 2003 (Atochem) catalyst was charged. After about thirty minutes at over 200° F., 97.50 grams of N-methyl pyrrolidinone (NMP), followed by 18.33 grams (0.48 eq.) dimethylol propanoic acid (DMPA) were charged. The resultant mixture was allowed to react for about two hours, at about 190–200° F. The percent NCO remaining was then measured using a titration with dibutylamine (DBA) and HCl. The result is a finished prepolymer.

Extension Step 640 grams of the prepolymer were warmed to 158° F. and 16.35 grams triethyl amine (TEA) were charged to the batch. When the TEA was thoroughly mixed, 564.1 grams of the prepolymer were charged to a vessel containing 457.19 grams water at 76° F. 13.25 grams N-methyl pyrrolidinone (NMP) were charged to the batch and allowed to mix for 15 minutes. Chain extension was then accomplished by charging a blend containing 6.49 grams meta-xylene diamine (MXDA)/3.28 grams DETA/16.34 grams water. The result is the polymer product.

EXAMPLE V

Prepolymer Step

The following materials were charged to a reactor: Half of a total of 335.56 grams (0.25 eq.) Acclaim 3201 (Arco Chemical); 195.73 grams isophorone diisocyanate (IPDI); and 31.86 grams (0.54 eq.) dimethylol propanoic acid (DMPA). Heat was applied to raise the batch to approximately 187° F. and then turned off. At approximately 208° F., 39.63 additional grams of the Acclaim 3201 were charged to the reactor. At about 205° F., 5.42 additional grams of the Acclaim 3201 were charged to the reactor. At about 194° F., one drop FASCAT® 2003 was charged to the reactor. The remainder of the Acclaim 3201 was then charged to the reactor. At 210° F., 106.7 grams of a total 286.86 grams 67-3000 HNA (Pioneer Plastics) was charged to the reactor. Within about five minutes, the remainder of the 67-3000 HNA was charged to the reactor. Once the reaction reached about 196° F., another drop of FASCAT® 2003 was charged to the reactor. The resultant mixture was allowed to react for about a half hour, at about 190–200° F. The percent NCO remaining was then measured using a titration with dibutylamine (DBA) and HCl.

Extension Step 140 grams of the prepolymer were warmed to 148° F. They were then charged to a vessel containing 199.32 grams water and 4.36 grams TEA at 62° F. and allowed to mix for 15 minutes. Chain extension was then accomplished by charging a blend containing 1.11 grams MXDA/0.56 grams DETA/8.35 grams water. A small amount of 35% hydrazine (3.80 grams) was added to complete chain extension. The resultant polymer can be used or can be stored under a nitrogen cap.

EXAMPLE VI

The finished prepolymer of Example V was chain extended as shown below.

Extension Step

Approximately two hours after the prepolymer was formed, 140 grams of the prepolymer of Example V were warmed to 155° F. The prepolymer was then charged to a vessel containing 204.97 grams water and 4.36 grams TEA at 65° F. and allowed to mix for 15 minutes. Chain extension was then accomplished by charging 5.30 grams 35% hydrazine. The resultant product is a polymer.

EXAMPLE VII

Prepolymer Step

The following materials were charged to a reactor: 421.78 grams (0.400 eq.) 1043-35 (RUCO Polymer Corp.); 110.12 grams (0.105 eq.) Acclaim 3201 (Arco Chemical); 86.68 grams (1.20 eq.) TMDI; and 53.53 grams (0.70 eq.) isophorone diisocyanate (IPDI), warmed to about 207° F., followed by shutting off the heat. When the reactor reached about 214° F., one drop FASCAT® 2003 was charged to the reactor followed by 22.82 grams (0.495 eq.) dimethylol propanoic acid (DMPA). The resultant mixture was allowed to react for about one and one half hours, at about 200° F. The percent NCO remaining was then measured using a titration with dibutylamine (DBA) and HCl. The result is a finished prepolymer.

Extension Step

The finished prepolymer was warmed to 204° F. 306.7 grams of the prepolymer were charged to a vessel containing 284.38 grams of water at 71° F. and allowed to mix for 15 minutes. Chain extension was then accomplished by charging a blend containing 4.46 grams EDA/13.38 grams water. A blended mixture containing 0.53 grams EDA and 3 grams water was then charged to the reactor followed by charging 1.5 grams TEA to the reactor. The result was a polymer.

EXAMPLES VIII–XIV

Each of the polyurethane dispersions of Examples I–VII was drawn down on Mylar® made of polyethylene terepthalate at approximately 8 wet mils and through-dried at ambient temperature. The Mylar® and polyurethane were then dried for three minutes at 300° F. in an oven. After drying, a 24-hour delay passed to allow the polyurethane to equilibrate at ambient temperature. The Mylar® was then cut into 1 inch wide strips. The dried polyurethane film was removed from the Mylar® and its thickness was measured.

Samples of the cured polyurethane film were then tested in the Instron tensile to measure various properties, including tensile strength, percentage elongation, and modulus. The interface type of the Instron was a Series 42/43/4400. The machine parameters of the test were set at a sample rate of 10 cm/sec and a cross-set speed of 2 in./min. Humidity was at 50% and the ambient temperature was 72° F.

Measurements of tensile strength at breaking, percentage elongation, and modulus of elasticity corresponding to samples of polyurethane film cast from the polyurethane dispersions of Examples I–VII are recorded in TABLES II-A through VIII-B below.

TABLE II-A

| DIMENSIONS | SPECIMEN 1[a] | SPECIMEN 2[a] |
|---|---|---|
| WIDTH (in.) | 1.0000 | 1.0000 |
| THICKNESS (in.) | .00270 | .00290 |
| SPEC. GAUGE LEN (in.) | 2.0000 | 2.0000 |
| GRIP DISTANCE (in.) | 2.0000 | 2.0000 |

[a]Specimens 1 and 2 correspond to a film cast from the polyurethane dispersion of Example I.

TABLE II-B

| | SPECIMEN 1[a] | SPECIMEN 2[a] |
|---|---|---|
| TENSILE AT MAX LOAD (psi) | 4826 | 4334 |
| ELONGATION (%) | 767.5 | 740.0 |
| STRESS AT 10% ELONGATION (psi) | 146.2 | 149.1 |
| STRESS AT 50% ELONGATION (psi) | 288.3 | 276.5 |
| STRESS AT 100% ELONGATION (psi) | 352.0 | 331.0 |
| STRESS AT 300% ELONGATION (psi) | 603.1 | 538.6 |
| STRESS AT 400% ELONGATION (psi) | 851.0 | 795.6 |
| STRESS AT 500% ELONGATION (psi) | 1264 | 1212 |

[a]Specimens 1 and 2 correspond to a film cast from the polyurethane dispersion of Example I.

TABLE III-A

| DIMENSIONS | SPECIMEN 1[a] | SPECIMEN 2[a] |
|---|---|---|
| WIDTH (in.) | 1.0000 | 1.0000 |
| THICKNESS (in.) | .00270 | .00270 |
| SPEC. GAUGE LEN (in.) | 2.000 | 2.000 |
| GRIP DISTANCE (in.) | 2.000 | 2.000 |

[a]Specimens 1 and 2 correspond to a film cast from the polyurethane dispersion of Example II.

TABLE III-B

| | SPECIMEN 1[a] | SPECIMEN 2[a] |
|---|---|---|
| TENSILE AT MAX LOAD (psi) | 4037 | 4419 |
| ELONGATION (%) | 767.0 | 797.5 |
| STRESS AT 10% ELONGATION (psi) | 113.3 | 107.4 |
| STRESS AT 50% ELONGATION (psi) | 240.6 | 226.7 |
| STRESS AT 100% ELONGATION (psi) | 298.3 | 280.4 |

TABLE III-B-continued

| | SPECIMEN 1[a] | SPECIMEN 2[a] |
|---|---|---|
| STRESS AT 300% ELONGATION (psi) | 524.1 | 485.6 |
| STRESS AT 400% ELONGATION (psi) | 740.5 | 697.1 |
| STRESS AT 500% ELONGATION (psi) | 1096.0 | 1049.0 |

[a]Specimens 1 and 2 correspond to a film cast from the polyurethane dispersion of Example II.

TABLE IV-A

| DIMENSIONS | SPECIMEN 1[a] | SPECIMEN 2[a] |
|---|---|---|
| WIDTH (in.) | 1.0000 | 1.0000 |
| THICKNESS (in.) | .00250 | .00280 |
| SPEC. GAUGE LEN (in.) | 2.0000 | 1.0000 |
| GRIP DISTANCE (in.) | 2.0000 | 1.0000 |

[a]Specimens 1 and 2 correspond to a film cast from the polyurethane dispersion of Example III.

TABLE IV-B

| | SPECIMEN 1[a] | SPECIMEN 2[a] |
|---|---|---|
| TENSILE AT MAX LOAD (psi) | 4812 | 4771 |
| ELONGATION (%) | 756.0 | 870.4 |
| STRESS AT 10% ELONGATION (psi) | 121.8 | 161.1 |
| STRESS AT 50% ELONGATION (psi) | 245.2 | 294.7 |
| STRESS AT 100% ELONGATION (psi) | 318.3 | 371.4 |
| STRESS AT 300% ELONGATION (psi) | 616.0 | 660.3 |
| STRESS AT 400% ELONGATION (psi) | 851.7 | 827.8 |
| STRESS AT 500% ELONGATION (psi) | 1242 | 1120 |

[a]Specimens 1 and 2 correspond to a film cast from the polyurethane dispersion of Example III.

TABLE V-A

| DIMENSIONS | SPECIMEN 1[a] |
|---|---|
| WIDTH (in.) | 1.0000 |
| THICKNESS (in.) | .00300 |
| SPEC. GAUGE LEN (in.) | 2.0000 |
| GRIP DISTANCE (in.) | 2.0000 |

[a]Specimen 1 corresponds to a film cast from the polyurethane dispersion of Example IV.

TABLE V-B

| | SPECIMEN 1[a] |
|---|---|
| TENSILE AT MAX LOAD (psi) | 4393 |
| ELONGATION (%) | 726.5 |
| STRESS AT 10% ELONGATION (psi) | 148.9 |
| STRESS AT 50% ELONGATION (psi) | 282.7 |
| STRESS AT 100% ELONGATION (psi) | 359.7 |
| STRESS AT 300% ELONGATION (psi) | 688.2 |
| STRESS AT 400% ELONGATION (psi) | 906.2 |
| STRESS AT 500% ELONGATION (psi) | 1312 |

[a]Specimen 1 corresponds to a film cast from the polyurethane dispersion of Example IV.

TABLE VI-A

| DIMENSIONS | SPECIMEN 1[a] |
|---|---|
| WIDTH (in.) | 1.0000 |
| THICKNESS (in.) | .00190 |

TABLE VI-A-continued

| DIMENSIONS | SPECIMEN 1[a] |
|---|---|
| SPEC. GAUGE LEN (in.) | 1.0000 |
| GRIP DISTANCE (in.) | 1.0000 |

[a]Specimen 1 corresponds to a film cast from the polyurethane dispersion of Example V.

TABLE VI-B

| | SPECIMEN 1[a] |
|---|---|
| TENSILE AT MAX LOAD (psi) | 5621 |
| ELONGATION (%) | 1030 |
| STRESS AT 10% ELONGATION (psi) | 135.6 |
| STRESS AT 50% ELONGATION (psi) | 281.8 |
| STRESS AT 100% ELONGATION (psi) | 350.4 |
| STRESS AT 300% ELONGATION (psi) | 627.1 |
| STRESS AT 400% ELONGATION (psi) | 853.1 |
| STRESS AT 500% ELONGATION (psi) | 1130 |

[a]Specimen 1 corresponds to a film cast from the polyurethane dispersion of Example V.

TABLE VII-A

| DIMENSIONS | SPECIMEN 1[a] | SPECIMEN 2[a] |
|---|---|---|
| WIDTH (in.) | 1.0000 | 1.0000 |
| THICKNESS (in.) | .00190 | .00200 |
| SPEC. GAUGE LEN (in.) | 1.0000 | 1.0000 |
| GRIP DISTANCE (in.) | 1.0000 | 1.0000 |

[a]Specimens 1 and 2 correspond to a film cast from the polyurethane dispersion of Example VI.

TABLE VII-B

| | SPECIMEN 1[a] | SPECIMEN 2[a] |
|---|---|---|
| TENSILE AT MAX LOAD (psi) | 5947.0 | 5870.0 |
| ELONGATION (%) | 1195.0 | 1190.0 |
| STRESS AT 10% ELONGATION (psi) | 129.3 | 123.8 |
| STRESS AT 50% ELONGATION (psi) | 283.2 | 263.1 |
| STRESS AT 100% ELONGATION (psi) | 366.7 | 329.0 |
| STRESS AT 300% ELONGATION (psi) | 594.5 | 548.6 |
| STRESS AT 400% ELONGATION (psi) | 755.0 | 715.0 |
| STRESS AT 500% ELONGATION (psi) | 961.9 | 922.7 |

[a]Specimens 1 and 2 correspond to a film cast from the polyurethane dispersion of Example VI.

TABLE VIII-A

| DIMENSIONS | SPECIMEN 1[a] |
|---|---|
| WIDTH (in.) | 1.0000 |
| THICKNESS (in.) | .00410 |
| SPEC. GAUGE LEN (in.) | 1.0000 |
| GRIP DISTANCE (in.) | 1.0000 |

[a]Specimen 1 corresponds to a film cast from the polyurethane dispersion of Example VII.

TABLE VIII-B

| | SPECIMEN 1[a] |
|---|---|
| TENSILE AT MAX LOAD (psi) | 4854 |
| ELONGATION (%) | 1715.00 |
| STRESS AT 10% ELONGATION (psi) | 90.37 |
| STRESS AT 50% ELONGATION (psi) | 205.6 |

TABLE VIII-B-continued

| | SPECIMEN 1[a] |
|---|---|
| STRESS AT 100% ELONGATION (psi) | 255.4 |
| STRESS AT 300% ELONGATION (psi) | 378.5 |
| STRESS AT 400% ELONGATION (psi) | 436.1 |
| STRESS AT 500% ELONGATION (psi) | 498.9 |

[a]Specimen 1 corresponds to a film cast from the polyurethane dispersion of Example VII.

As can be appreciated, the present invention is useful for a wide array of products that can be simply and economically manufactured using an elastomeric film cast or dipped from a waterborne polyurethane dispersion or by using the polymer, i.e., the waterborne polyurethane dispersion, as a coating for textiles, such as backcoatings, fabric or fiber saturants, finishes, or transfer coatings, or other textile and non-textile applications where good elastomeric properties would be useful. The film can be prepared in the absence of a solvent, thus making it attractive for a variety of protection products for medical and industrial applications such as gloves, condoms, catheters, and the like.

The invention has been described with reference to preferred and alternate embodiments. Obviously, modifications and alterations will occur to others upon the reading and understanding of this specification. It is intended to include all such modifications and alterations insofar as they come within the scope of the appended claims or the equivalents thereof

Having thus described the preferred embodiments, the invention is claimed as follows:

1. A waterborne polyurethane dispersion wherein the polyurethane comprises the reaction product of
    (a) a polyisocyanate component selected from the group consisting of an aliphatic polyisocyanate, an aromatic polyisocyanate, a cycloaliphatic polyisocyanate, and an aralphatic polyisocyanate;
    (b) a long-chain, active hydrogen containing material, containing 2 or more active hydrogens per molecule selected from the group consisting of a polyamide, a polyester polyol, a polyether polyol and mixtures thereof, having an average molecular weight from about 2900 to about 5500 Daltons, and being a liquid at 90° F. or lower; and
    (c) a water-solubilizing compound having water-solubilizing groups selected from the group consisting of dimethylol propanoic acid, tartaric acid, dimethylol butanoic acid, glycollic acid, thioglycollic acid, lactic acid, malic acid, dihydroxymalic acid, dihydroxytartaric acid, and 2,6-dihydroxybenzoic acid and present in a range of from about 2 wt. % to about 4 wt. % of the total prepolymer,
    to form an isocyanate prepolymer, having a NCO to OH ratio of about 1.3/1 to about 4.0/1, which is neutralized by reaction with a tertiary amine, dispersed in water, and chain extended by reaction with an amine, said polyurethane dispersion, when in the form of a film, having elastic properties comparable to rubber, a tensile strength greater than about 3500 psi, a 100% modulus below 450 psi, a 500% modulus below 1500 psi, and a percentage elongation greater than about 700% at 72° F.

2. The polyurethane dispersion of claim 1 wherein the polyisocyanate is a diisocyanate.

3. The polyurethane dispersion of claim 1 wherein the NCO to OH ratio of the prepolymer is about 1.4/1 to about 3.0/1.

4. The polyurethane dispersion of claim 1 wherein the NCO to OH ratio of the prepolymer is about 1.8/1 to about 2.3/1.

5. The polyurethane dispersion of claim 1 wherein the NCO to OH ratio of the prepolymer is about 1.9/1 to about 2.1/1.

6. The polyurethane dispersion of claim 2 wherein the diisocyanate is one selected from the group consisting of isophorone diisocyanate, 2,2,4 trimethyl hexamethylene, 2,4,4 trimethyl hexamethylene and mixtures thereof.

7. The polyurethane dispersion of claim 2 wherein the diisocyanate is one selected from the group consisting of tetramethylxylene diisocyanate(TMXDI), cyclohexyl bis-methylenisocyanate($H_{12}$MDI), methane-bis(4-phenyl isocyanate)(MDI), toluene diisocyanate (TDI), 2,2,4 and 2,4,4 isomer blend of trimethyl hexamethylene diisocyanate (TMDI) and mixtures thereof.

8. The polyurethane dispersion of claim 1 wherein the polyester polyol is one selected from the group consisting of a hexanediol neopentyl glycol adipate, ethylene glycol/diethylene glycol adipate, and ethylene glycol/butane diol adipate, and mixtures thereof.

9. The polyurethane dispersion of claim 1 wherein the polyether polyol is one selected from the group consisting of poly-ethylene oxide, poly-propylene oxide, and mixtures thereof.

10. The polyurethane dispersion of claim 1 wherein the long-chain amine is an amine-terminated polypropylene glycol.

11. The polyurethane dispersion of claim 1 wherein the water-solubilizing compound is one selected from the group consisting of dimethylol propanoic acid, tartaric acid, dimethylol butanoic acid, glycollic acid, thioglycollic acid, lactic acid, malic acid, dihydroxymalic acid, dihydroxytartaric acid, and 2,6-dihydroxybenzoic acid.

12. The polyurethane dispersion of claim 1 wherein the water-solubilizing compound is dimethylol propanoic acid.

13. The polyurethane dispersion of claim 1 wherein the amine for chain extension is one selected from the group consisting of primary amines, secondary amines, inorganic amines and mixtures thereof.

14. The polyurethane dispersion of claim 1 wherein the amine for chain extension is one selected from the group consisting of diethylenetriamine, ethylene diamine, meta-xylylenediamine, aminoethylethanolamine, hydrazine and mixtures thereof.

15. The polyurethane dispersion of claim 1 wherein the tertiary amine is one selected from the group consisting of triethylamine, dimethylethanol amine, and N-methylmorpholine.

16. The polyurethane dispersion of claim 1 wherein the film further comprises a 100% modulus below 400 psi, a 300% modulus below 700 psi, and, a 500% modulus below 1500 psi at 72° F.

17. The polyurethane dispersion of claim 1 wherein the polyurethane is prepared in the absence of a solvent.

18. A waterborne polyurethane for use as a film having elastomeric properties, said film having a tensile strength greater than about 3500 psi, a 100% modulus below 450 psi, a percentage elongation greater than 700%, and being able to be stretched at room temperature to at least twice its original length and return to approximately its original length within a short time.

19. The polyurethane of claim 18 wherein the polyurethane comprises the reaction product of
(a) a polyisocyanate component;
(b) a long-chain polyol or a long-chain amine; and,
(c) a water-solubilizing compound having water-solubilizing groups to form an isocyanate prepolymer, which is neutralized by reaction with a tertiary amine, dispersed in water, and chain extended by reaction with an amine.

20. The polyurethane of claim 19 wherein the polyisocyanate is one selected from the group consisting of an aliphatic polyisocyanate, an aromatic polyisocyanate, a cycloaliphatic polyisocyanate, and an araliphatic polyisocyanate.

21. The polyurethane of claim 19 wherein the polyisocyanate is a diisocyanate.

22. The polyurethane of claim 21 wherein the NCO to OH ratio of the prepolymer is about 1.8/1 to about 2.3/1.

23. The polyurethane of claim 21 wherein the diisocyanate is one selected from the group consisting of 2,2,4 trimethyl, hexamethylene, isophorone diisocyanate, 2,4,4 trimethyl hexamethylene and mixtures thereof.

24. The polyurethane of claim 21 wherein the diisocyanate is one selected from the group consisting tetramethylxylene diisocyanate(TMXDI), cyclohexyl bis-methylenisocyanate($H_{12}$MDI), methane-bis(4phenyl isocyanate)(MDI), toluene diisocyanate (TDI), 2,4,4 trimethyl hexamethylene diisocyanate (TMDI) and mixtures thereof.

25. The polyurethane of claim 19 wherein the long-chain polyol is one selected from the group consisting of a polycarbonate polyol, a polyester polyol, a polyether polyol and mixtures thereof.

26. The polyurethane of claim 25 wherein the polyester polyol is one selected from the group consisting of a ethylene glycol/diethylene glycol adipate, hexane diol neopentyl glycol adipic acid, and ethylene glycol/butane diol adipate, and mixtures thereof.

27. The polyurethane of claim 19 wherein the long-chain polyol has an average molecular weight from about 2900 to about 5500 Daltons.

28. The polyurethane of claim 25 wherein the polyether polyol is one selected from the group consisting of poly-ethylene oxide, poly-propylene oxide, and mixtures thereof.

29. The polyurethane of claim 19 wherein the long-chain amine is an amine-terminated polypropylene glycol.

30. The polyurethane of claim 19 wherein the water-solubilizing compound is one selected from the group consisting of dimethylol propanoic acid, tartaric acid, dimethylol butonic acid, glycollic acid, thioglycollic acid, lactic acid, malic acid, dihydroxymalic acid, dihydroxytartaric acid, and 2,6-dihydroxybenzoic acid.

31. The polyurethane of claim 19 wherein the water-solubilizing compound is present in a range of from about 2 wt. % to about 4 wt. % of the total prepolymer.

32. The polyurethane of claim 19 wherein the water-solubilizing compound is dimethylol propanoic acid.

33. The polyurethane of claim 19 wherein the amine for chain extension is one selected from the group consisting of primary amines, secondary amines, inorganic amines and mixtures thereof.

34. The polyurethane of claim 19 wherein the amine for chain extension is one selected from the group consisting of diethylenetriamine, ethylenediamine, meta-xylylenediamine, aminoethylethanolamine, hydrazine and mixtures thereof.

35. The polyurethane of claim 19 wherein the tertiary amine is one selected from the group consisting of triethylamine, dimethylethanol amine, and N-methylmorpholine.

36. The polyurethane of claim 19 wherein the film further comprises a 100% modulus below 450 psi, a 300% modulus below 700 psi, and a 500% modulus below 1500 psi at 72° F.

37. The polyurethane of claim 19 wherein the polyurethane is prepared in the absence of a solvent.

38. A film cast from a waterborne polyurethane dispersion, said film having a percentage elongation greater than 700%, a 100% modulus below 450 psi, a tensile strength greater than about 3500 psi, and being able to be stretched at room temperature to at least twice its original length and return to approximately its original length within a short time.

39. The film of claim 38, wherein said polyurethane comprises the reaction product of
  (a) a polyisocyanate component;
  (b) a long-chain polyol, polyamine, or other active hydrogen containing material, containing 2 or more active hydrogens per molecule; and
  (c) a water-solubilizing compound having water-solubilizing groups
  to form an isocyanate prepolymer, which is neutralized by reaction with a tertiary amine, dispersed in water, and chain extended by reaction with an amine.

40. The film of claim 39 wherein the polyisocyanate is one selected from the group consisting of an aliphatic polyisocyanate, an aromatic polyisocyanate, a cycloaliphatic polyisocyanate, and an araliphatic polyisocyanate.

41. The film of claim 39 wherein the polyisocyanate is a diisocyanate.

42. The polyurethane dispersion of claim 39 wherein the NCO to OH ratio of the prepolymer is about 1.8/1 to about 2.3/1.

43. The film of claim 41 wherein the diisocyanate is one selected from the group consisting of isophorone diisocyanate and isomer blends of trimethyl hexamethylene diisocyanate.

44. The film of claim 41 wherein the diisocyanate is one selected from the group consisting tetramethylxylene diisocyanate(TMXDI), cyclohexyl bis-methylenisocyanate ($H_{12}$MDI), methane-bis(4-phenyl isocyanate)(MDI), toluene diisocyanate (TDI), 2,2,4 and 2,4,4 isomer blend of trimethyl hexamethylene diisocyanate (TMDI) and mixtures thereof.

45. The film of claim 39 wherein the long-chain polyol is one selected from the group consisting of a polyester polyol, a polyether polyol and mixtures thereof.

46. The film of claim 45 wherein the polyester polyol is one selected from the group consisting of a hexane diol neopentyl glycol aditate, ethylene glycol/diethylene glycol adipate, and mixtures thereof.

47. The film of claim 39 wherein the long-chain polyol has an average molecular weight from about 2900 to about 5500 Daltons.

48. The polyurethane dispersion of claim 45 wherein the polyether polyol is one selected from the group consisting of poly-ethylene oxide, poly-propylene oxide, and mixtures thereof.

49. The polyurethane dispersion of claim 39 wherein the long-chain amine is an amine-terminated polypropylene glycol.

50. The film of claim 39 wherein the water-solubilizing compound is one elected from the group consisting of dimethylol propanoic acid, tartaric acid, dimethylol butanoic acid, glycollic acid, thioglycollic acid, lactic acid, malic acid, dihydroxymalic acid, dihydroxytartaric acid, and 2,6-dihydroxybenzoic acid.

51. The polyurethane dispersion of claim 39 wherein the water-solubilizing compound is present in a range from about 2 wt. % to about 4 wt. % of the total prepolymer.

52. The film of claim 39 wherein the water-solubilizing compound is dimethylol propanoic acid.

53. The film of claim 39 wherein the amine for chain extension is one selected from the group consisting of primary amines, secondary amines, inorganic amines and mixtures thereof.

54. The film of claim 39 wherein the amine for chain extension is one selected from the group consisting of diethylene triamine, ethylene diamine, meta-xylylenediamine, aminoethylethanolamine, hydrazine and mixtures thereof.

55. The film of claim 39 wherein the tertiary amine is one selected from the group consisting of triethylamine, dimethylethanol amine, and N-methylmorpholine.

56. The film of claim 38 wherein the film further comprises a 300% modulus below 700 psi and a 500% modulus below 1500 psi at 72° F.

57. The film of claim 39 wherein the film is prepared in the absence of a solvent.

58. Medical gloves comprising the film of claim 38.

59. Contraceptive devices comprising the film of claim 38.

60. A catheter comprising the film of claim 38.

61. A waterborne polyurethane dispersion according to claim 1 wherein the polyisocyanate component is selected from the group consisting of isophorone diisocyanate, hexamethylene 1,6-diisocyanate, 1,12-dodecane diisocyanate, 2,2,4-trimethyl-hexamethylene diisocyanate, 2,4,4-trimethyl-hexamethylene diisocyanate, 2-methyl-1,5-pentamethylene diisocyanate, 2,2,4 and 2,4,4 isomer blend of trimethyl hexamethylene diisocyanate and mixtures thereof;
  the long-chain, active hydrogen containing material is a polyester polyol having an average molecular weight from about 2900 to about 5500 Daltons, and being a liquid at 90° F. or lower; and
  the water-solubilizing compound is selected from the group consisting of dimethylol propanoic acid, tartaric acid, dimethylol butanoic acid, glycollic acid, thioglycollic acid, lactic acid, malic acid, dihydroxymalic acid, dihydroxytartaric acid, and 2,6-dihydroxybenzoic acid and present in a range of from about 2 wt. % to about 4 wt. % of the total prepolymer; and
  the NCO to OH ratio is about 1.8/1 to about 2.3/1.

* * * * *